(12) United States Patent
Lucic et al.

(10) Patent No.: US 9,176,030 B2
(45) Date of Patent: Nov. 3, 2015

(54) SUBSTRATE AND TARGET PLATE

(75) Inventors: Ivan Lucic, Vienna (AT); Peter Hausberger, Radfeld (AT); Werner Balika, Seekirchen am Wallersee (AT); Christian Poeschl, Neumarkt (AT)

(73) Assignee: SONY DADC Austria AG, Anif (AT)

( * ) Notice: Subject to any disclaimer, the term of this patent is extended or adjusted under 35 U.S.C. 154(b) by 681 days.

(21) Appl. No.: 12/408,082

(22) Filed: Mar. 20, 2009

(65) Prior Publication Data

US 2009/0246470 A1 Oct. 1, 2009

(30) Foreign Application Priority Data

Mar. 31, 2008 (EP) .................................... 08006553

(51) Int. Cl.
| | |
|---|---|
| *B32B 3/00* | (2006.01) |
| *G01N 1/28* | (2006.01) |
| *B01L 3/00* | (2006.01) |
| *H01J 49/04* | (2006.01) |
| *G01N 1/40* | (2006.01) |

(52) U.S. Cl.
CPC ............ *G01N 1/2813* (2013.01); *B01L 3/5085* (2013.01); *H01J 49/0418* (2013.01); *B01L 2300/16* (2013.01); *B01L 2300/163* (2013.01); *G01N 2001/4027* (2013.01); *Y10T 428/24479* (2015.01)

(58) Field of Classification Search
CPC .............. B01L 3/5085; B01L 2300/16; B01L 2300/163; G01N 2001/4027; G01N 1/2813
USPC ........................................................ 428/156
See application file for complete search history.

(56) References Cited

U.S. PATENT DOCUMENTS

| | | | |
|---|---|---|---|
| 2004/0023287 A1 | 2/2004 | Harnack et al. | |
| 2004/0067339 A1* | 4/2004 | Gandon et al. | ................. 428/141 |
| 2004/0219531 A1 | 11/2004 | DiCesare | |
| 2006/0078724 A1* | 4/2006 | Bhushan et al. | .............. 428/323 |
| 2007/0013106 A1 | 1/2007 | Lee et al. | |
| 2007/0031639 A1* | 2/2007 | Hsu et al. | ....................... 428/141 |
| 2007/0202602 A1 | 8/2007 | DeLucas et al. | |
| 2007/0227428 A1* | 10/2007 | Brennan et al. | ............. 114/67 R |
| 2008/0055581 A1* | 3/2008 | Rogers et al. | ................... 355/95 |

FOREIGN PATENT DOCUMENTS

| | | |
|---|---|---|
| CN | 1760112 A | 4/2006 |
| DE | 101 34 362 A1 | 1/2003 |
| DE | 101 38 036 A1 | 2/2003 |

(Continued)

OTHER PUBLICATIONS

U.S. Appl. No. 12/852,841, filed Aug. 9, 2010, Lucic, et al.

(Continued)

*Primary Examiner* — Maria Veronica Ewald
*Assistant Examiner* — Laura Auer
(74) *Attorney, Agent, or Firm* — Oblon, McClelland, Maier & Neustadt, L.L.P.

(57) ABSTRACT

A substrate is provided, which comprises a structured surface including a regular pattern of a plurality of elevated structures that are elevated with respect to a nominal surface of the substrate, wherein at least two dimensions are between 1 nm and 100 μm, the structured surface being configured to stimulate smooth crystallization of microcrystals or to boost hydrophobic properties. A target plate comprising a plurality of substrates is disclosed as well.

25 Claims, 11 Drawing Sheets

(56) References Cited

FOREIGN PATENT DOCUMENTS

| | | |
|---|---|---|
| EP | 1 284 495 A2 | 2/2003 |
| EP | 1 830 184 A1 | 9/2007 |
| JP | 2004-184137 A | 7/2004 |
| JP | 2006-525520 A | 11/2006 |
| TW | I261615 | 9/2006 |
| WO | WO 01/92293 A2 | 6/2001 |
| WO | WO 03/069028 A1 | 8/2003 |
| WO | WO 2004/100207 A2 | 11/2004 |
| WO | WO 2006/046697 A1 | 5/2006 |

OTHER PUBLICATIONS

Office Action issued Jan. 29, 2013 in Japanese Patent Application No. 2009-086435 with English language translation.

* cited by examiner

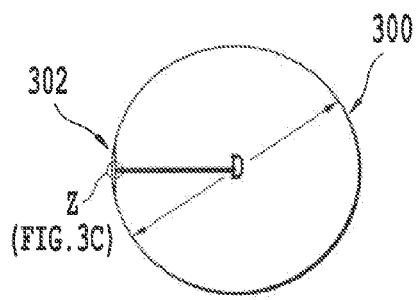
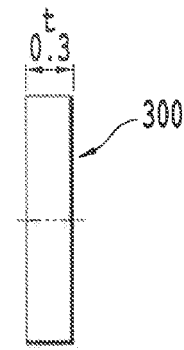
*Fig.3A*  *Fig.3B*
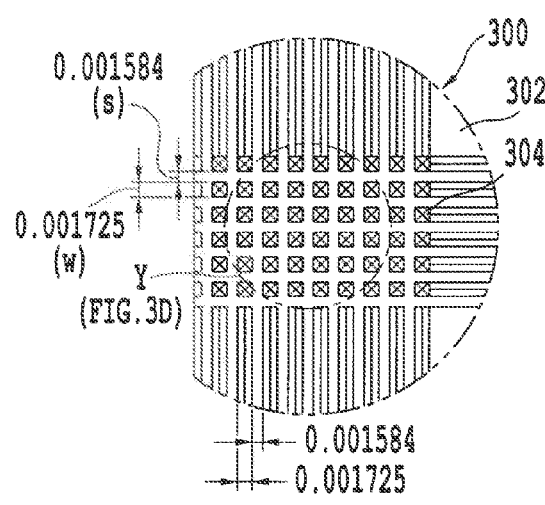
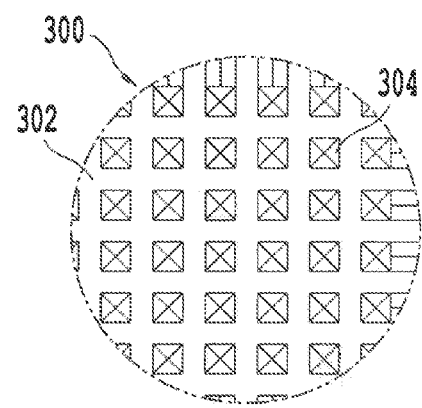
*Fig.3C*  *Fig.3D*

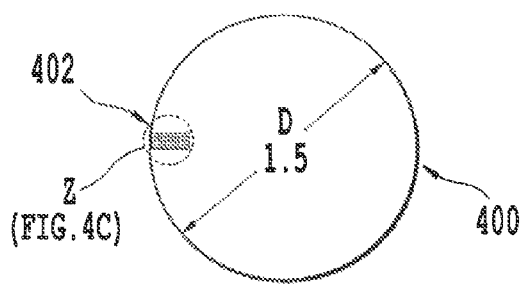
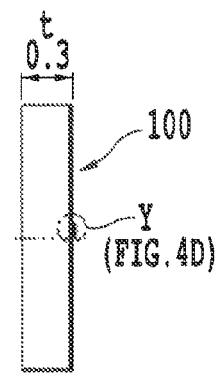
Fig.4A  Fig.4B
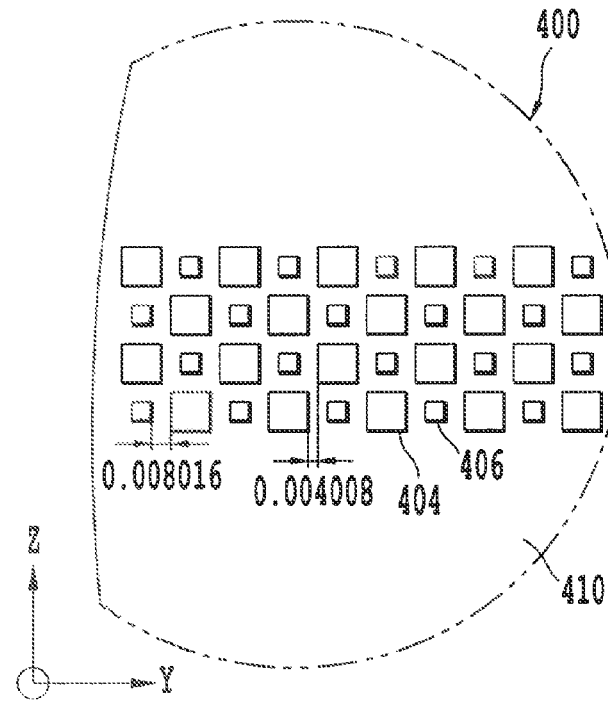
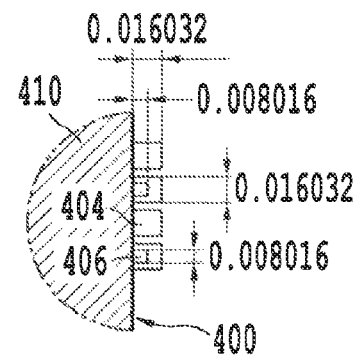
Fig.4D
Fig.4C
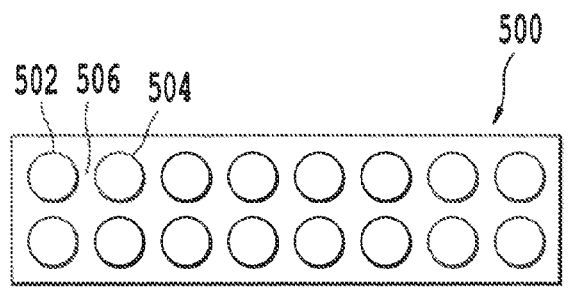
Fig.5

| Crystallization |  |  |
|---|---|---|
| | unsmooth | smooth |
| Polymer | polypropylene | polypropylene |
| Coating | diamond-like carbon | - |
| Structured surface | no | yes |

Same sample preparation in both cases (mix of matrix, analyte and solvents; drop volume of 0.5 µl)

| COMPOUND | OTHER NAMES | SOLVENT | WAVE LENGTH (nm) | APPLICATIONS |
|---|---|---|---|---|
| 2,5-dihydroxy benzoic acid[1] | DHB, Gentisic acid | acetonitrile, water, methanol, acetone, chloroform | 337, 355, 266 | peptides, nucleotides, oligonucleotides, oligosaccharides |
| 3,5-dimethoxy-4-hydroxycinnamic acid[2][3] | sinapic acid; sinapinic acid; SA | acetonitrile, water, acetone, chloroform | 337, 355, 266 | peptides, proteins, lipids |
| 4-hydroxy-3-methoxycinnamic acid[2][3] | ferulic acid | acetonitrile, water, propanol | 337, 355, 266 | proteins |
| α-cyano-4-hydroxycinnamic acid[4] | CHCA | acetonitrile, water, ethanol, acetone | 337, 355 | peptides, lipids, nucleotides |
| Picolinic acid[5] | PA | Ethanol | 266 | oligonucleotides |
| 3-hydroxy picolinic acid[6] | HPA | Ethanol | 337, 355 | oligonucleotides |

*Fig. 7*

SUBSTRATE AND TARGET PLATE

An embodiment of the invention relates to a substrate. A further embodiment relates to a target plate.

BACKGROUND

The wetting of a surface of a solid such as e.g. a polymer material, silicon, a metal or an alloy by a liquid indicates an interaction between the surface of the solid and a molecule of liquid (adsorption of liquid to the surface of a solid), and a competitive phenomenon of adhesion between the solid and liquid and cohesion between molecules of the liquid. A larger cohesion than adhesion brings about a decrease in wettability, and less cohesion than adhesion brings about an increase in wettability.

Good wettability to liquid water refers to hydrophilic properties, and poor wettability refers to hydrophobic properties.

Such wettability can be quantitatively determined by measuring a contact angle of a solid surface. The hydrophobic properties mainly depend on chemical properties of the surface and of the micro- and nano-structures thereof.

Various methods have been reported (e.g. in US 2007/0013106A1) to construct hydrophobic surfaces by modifying structures of the surfaces. Conventionally, hydrophobic surfaces are fabricated with the help of chemical treatment for changing the surface energy of materials or for modifying the surface roughness, for example by polypropylene etching, plasma enhanced chemical vapor deposition (PECVD), plasma polymerization, plasma fluorination of polybutadiene, microwave anodic oxidation of aluminum, solidification of an alkylketene dimer, nanostructuring carbon film, polypropylene coating, carbon nanotube aligning, forming poly(vinyl) alcohol nanofibers, making the surface of polydimethylsiloxane porous, or oxygen plasma treatment. US 2007/0013106 A1 in particular disclose a UV-nanoimprint lithography technique to produce a hydrophobic structure in a polymer film based on replicating the structure of a hydrophobic leaf, e.g. lovegrass leaf.

In Life Science diagnostics in order to analyze e.g. proteins, the proteins are solved in a liquid, also referred to as crystallization matrix and afterwards a droplet of the combination of crystallization matrix and protein, also referred to as analyte is applied on a surface of a substrate. The crystallization matrix evaporates and the protein/matrix alloy crystallize on the surface of the substrate. The crystallized proteins are then analyzed via e.g. a mass spectrometric process.

Known crystallization matrices have compounds like e.g. 2,5-dihydroxy benzoic acid, 3,5-dimethoxy-4-hydroxycinnamic acid, 4-hydroxy-3-methoxycinnamic acid, α-cyano-4-hydroxycinnamic acid, picolinic acid or 3-hydroxy picolinic acid and their respective solvents and applications are depicted in FIG. 7, which also show the used wavelength in the ultraviolet (UV)-region used for analytic purposes. Further matrices might be used as well, e.g. a polymer research matrix called "Dithranol".

BRIEF SUMMARY

It is an object of the invention to provide a substrate and a target plate for improving the analytic process.

This object is solved by a substrate and a target plate according to claims 1 and 20.

Further details of the invention will become apparent from a consideration of the drawings and ensuing description.

BRIEF DESCRIPTION OF THE SEVERAL VIEWS OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3a shows a top view on a substrate according to a third embodiment;

FIG. 3b shows a side view of a substrate according to the third embodiment;

FIG. 3c shows an enlarged section of the top view in FIG. 3a;

FIG. 3d shows an further enlarged detail of the top view in FIG. 3c,

FIG. 4a shows a top view on a substrate according to a fourth embodiment;

FIG. 4b shows a side view of a substrate according to the fourth embodiment;

FIG. 4c shows an enlarged detail of the top view in FIG. 4a;

FIG. 4d shows an enlarged detail of the side view in FIG. 4b,

FIG. 5 shows a top view on a target plate according to a further embodiment, FIG. 7 shows a table with known crystallization matrices and their application.

DETAILED DESCRIPTION

In the following, embodiments of the invention are described. It is important to note, that all described embodiments in the following may be combined in any way, i.e. there is no limitation that certain described embodiments may not be combined with others. Further, it should be noted that same reference signs throughout the figures denote same or similar elements.

It is to be understood that other embodiments may be utilized and structural or logical changes may be made without departing from the scope of the invention. The following detailed description, therefore, is not to be taken in a limiting sense, and the scope of the present invention is defined by the appended claims.

It is to be understood that the features of the various embodiments described herein may be combined with each other, unless specifically noted otherwise.

Figure 1A:
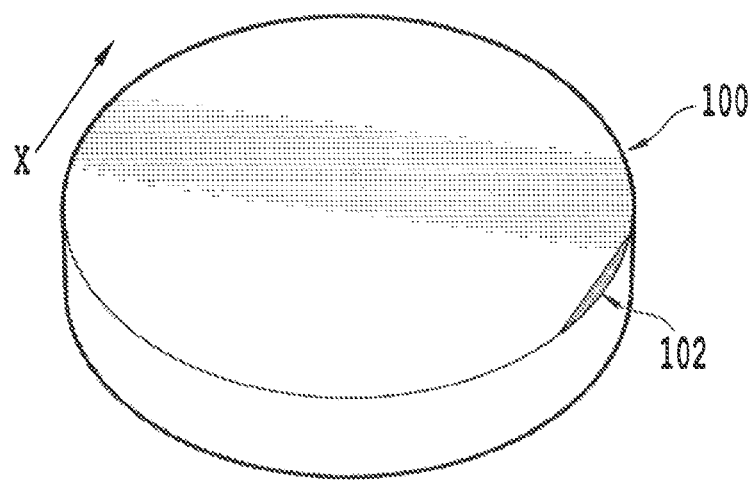
FIG. 1a shows a substrate according to a first embodiment.

In FIG. 1a a substrate 100 is depicted with a structured surface 102 according to a first embodiment of the invention. The substrate 100 might be a polymer, a treated polymer, a metal, an alloy or based on ceramics. The structured surface 102 might be realized by molding, embossing, etching, or any other surface structuring method known to a person skilled at the art.

Figure 1B:
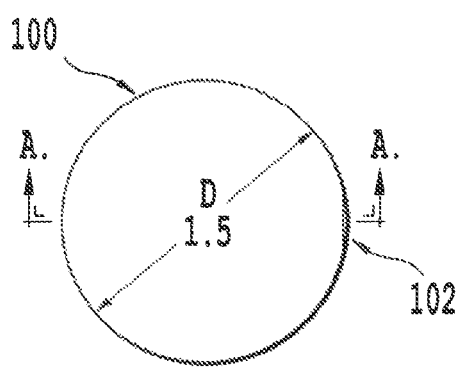
FIG. 1b shows a top view on a substrate according to the first embodiment.

As depicted in the top view of the substrate 100 in FIG. 1b a diameter D of the substrate 100 might be 1.5 mm. However, other diameters or shapes of the substrate are possible, e.g. squares, rectangle or irregular shapes. The substrates might even be layered or situated on top of irregularly formed items in order to provide a structured surface on these items.

Figure 1C:
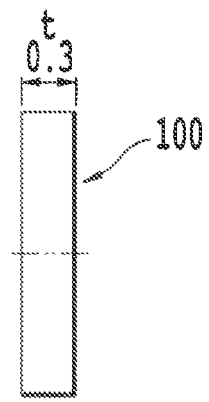
FIG. 1c shows a side view of a substrate according to the first embodiment.

In the side view depicted in FIG. 1c it is depicted that the thickness t of the substrate is 0.3 mm, however, other thicknesses are possible as well.

Figure 1D:
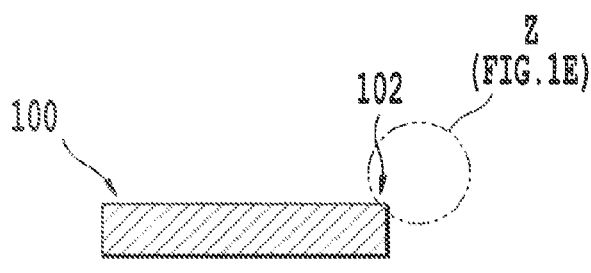
FIG. 1d shows a cross-section of a substrate according to the first embodiment along the intersection line A-A of FIG. 1b.
Figure 1E:
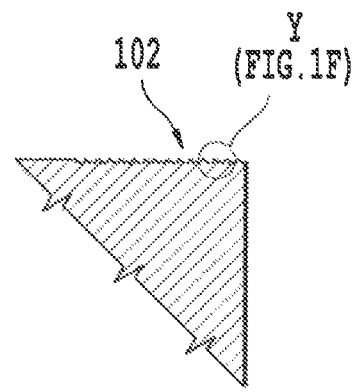
FIG. 1e shows an enlarged detail of the cross-section of FIG. 1d.
Figure 1F:
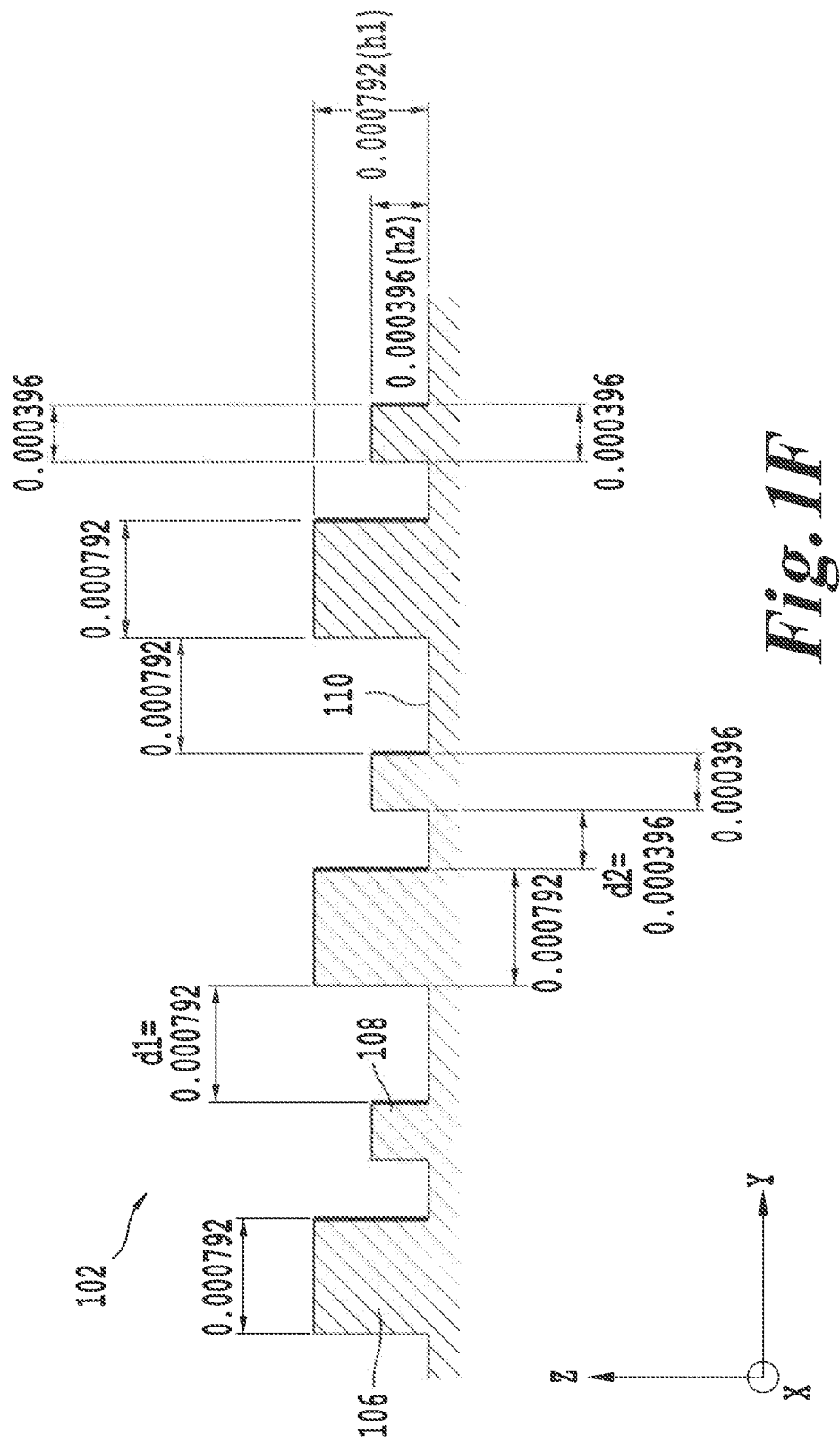
FIG. 1f shows a further enlarged detail of the cross-section of FIG. 1e.

In FIG. 1d a cross-section of the substrate along the intersection line A-A of FIG. 1a is depicted and in FIG. 1e an enlarged view of the cross-section in FIG. 1d, corresponding to the region labeled "Z" is depicted. A further enlarged detail is depicted in FIG. 1f or the region labeled "Y" in FIG. 1e.

Figure 1G:
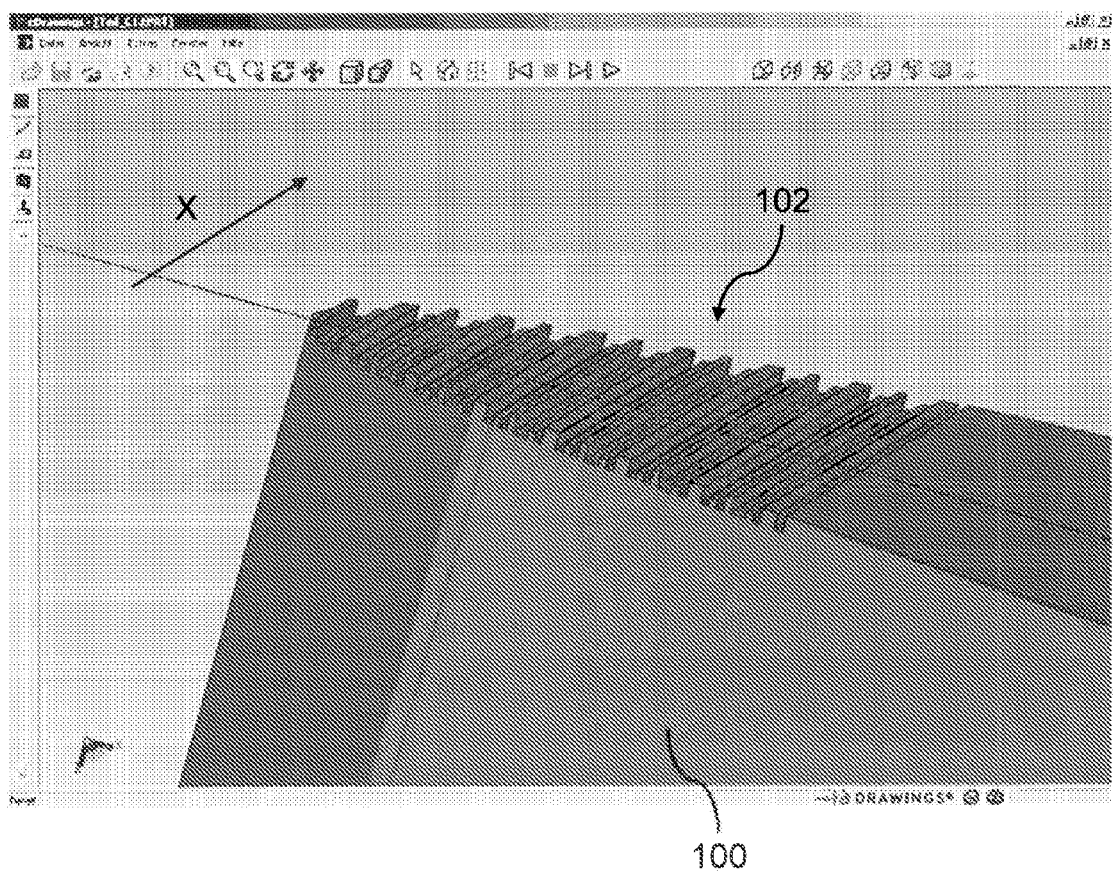
FIG. 1g shows a perspective view on a surface of a substrate according to the first embodiment.

FIG. 1g shows a perspective view of the structured surface 102 of the first embodiment. As it is depicted in FIGS. 1g and 1f most prominently, the structured surface 102 includes a regular pattern 104 of a plurality of elevated structures 106, 108, wherein at least two dimensions of the elevated structures 106, 108 are between 1 nm and 100 μm, preferably between 1 nm and 50 μm, more preferably between 1 nm and 2 μm. The elevated structures are elevated with respect to a nominal surface 110 of the substrate. Similar smooth crystallization effects are achievable when the structure is inverted, i.e. when the structures are not elevated with respect to a nominal surface but are trenches below the nominal surface.

Further on, the structured surface 102 is configured to stimulate a smooth crystallization of microcrystals, when a droplet of an analyte is applied on the substrate 100.

The structured surface 102, also referred to as microstructure, is simultaneously boosting the hydrophobic property of the substrate 100.

The nature, dimensions and forms of the structured surface 102 have been determined by taking into account size, crystallization form and shape of microcrystals as well as properties of the crystallization matrix and hydrophobic properties.

The regular or uniform pattern results in a uniform or smooth crystallization. Otherwise, microcrystallization of different fluids and crystallization-matrices at almost perfect even and glossy surfaces follow the rules of self-organization and shape tight dendritic or other mostly self-similar crystal forms, for instance as crystal arrangements as a dense layer of single crystals or chain-like clusters. These arrangements have random dispersion at almost perfect and even surfaces, resulting in a non-uniform signal in analyzing apparatuses, since e.g. a laser used for evaporating the microcrystals evaporates different amounts of the microcrystals due to the irregular microcrystal pattern on the surface of the substrates.

The regular pattern 104 of elevated structures 106, 108 increase the contact angle or coating angle of droplets on the surface 102, thereby decreasing an expansion of the matrix-droplets and decreasing the contact surface between analyte and substrate, and offering cores for crystallization for the used matrix. This leads to smoother and more homogeneous crystallization. Also the crystallization time is reduced, thus, increasing the throughput of analyzing apparatuses.

The substrate might be used for analyzing proteins in Life Sciences or in e.g. environmental/chemical analytics and forensics and for other analytes like polymers, sugars, lipids, metabolites, etc.

An additional surface treatment or a further surface chemistry is not necessary.

The first embodiment of the invention depicted in FIGS. 1a to 1g includes a basic unit of a first elevated structure 106 and a second elevated structure 108, which are elongated along a first direction x in parallel to the surface 102. The cross-section of the first elevated structure 106 is larger than the cross-section of the second elevated structure 108. The pattern of regularly repeating the basic unit of elongated structures or ridges with different cross-sections has been found to produce a very smooth crystallization.

The cross-section of the first elevated structures 106 and the second elevated structures 108 are depicted as squares, but might also be realized as rectangles.

A improved smoothness of crystallization has been achieved when in the pattern a first distance d1 between the first elevated structure 106 and the second elevated structure 108 is different from a second distance d2 between the second elevated structure 108 and the next first elevated structure 106.

A further improved pattern is achieved when the first distance d1 and a first side 11 of the first cross-section are equal in length and wherein the second distance d2 and a first side 12 of the second cross-section are equal in length. In FIG. 1f it is depicted that the first distance d1 equals 0.000792 mm and the second distance equals 0.000396 mm.

A further improved pattern results when a height h1 of the first cross-section perpendicular to the nominal surface 110 is twice a height h2 of the second cross-section perpendicular to the nominal surface 110. In FIG. 1f it is depicted that the height h1 might be 0.000792 mm and the height h2 might be 0.000392 mm.

Figure 2A:
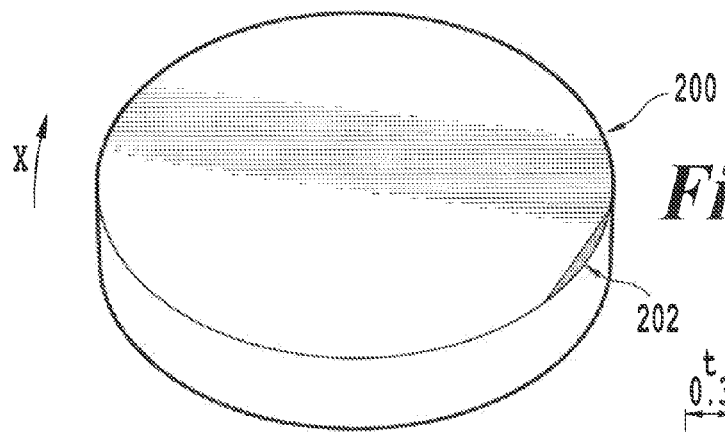
FIG. 2a shows a substrate according to a second embodiment.
Figure 2B:
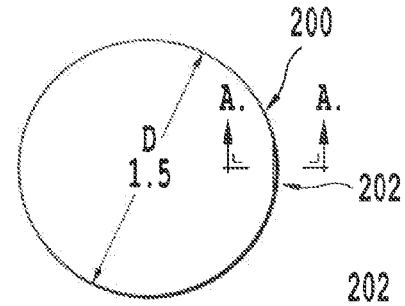
FIG. 2b shows a top view on a substrate according to the second embodiment.
Figure 2C:
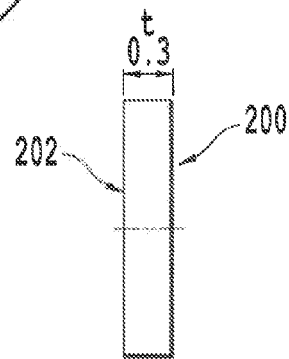
FIG. 2c shows a side view of a substrate according to the second embodiment.
Figure 2D:
FIG. 2d shows a cross-section of a substrate according to the second embodiment along the intersection line A-A of FIG. 2b.
Figure 2E:
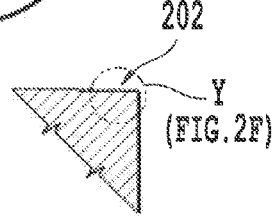
FIG. 2e shows an enlarged detail of the cross-section in FIG. 2d.
Figure 2F:
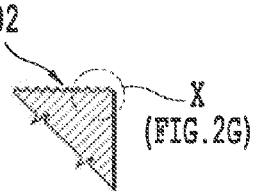
FIG. 2f shows a further enlarged detail of the cross-section in FIG. 2e.
Figure 2G:
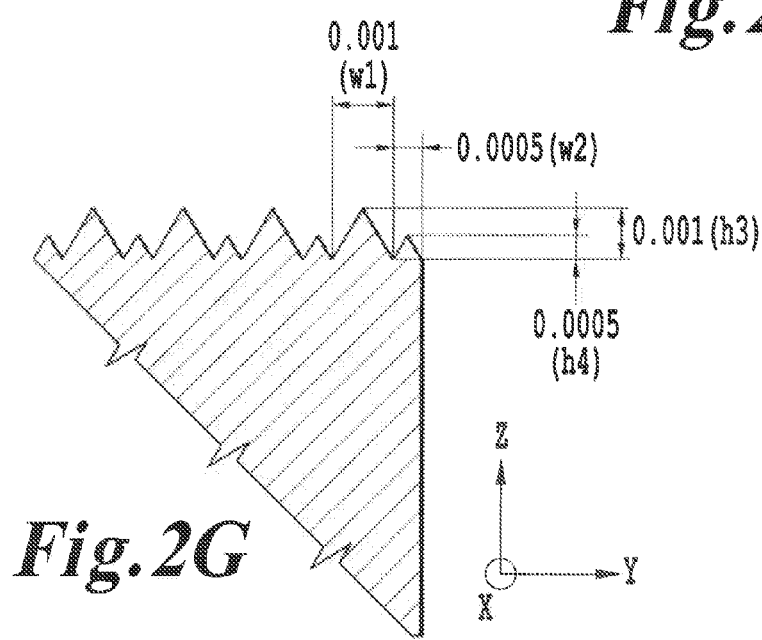
FIG. 2g shows a further enlarged detail of the cross-section in FIG. 2f
Figure 2H:
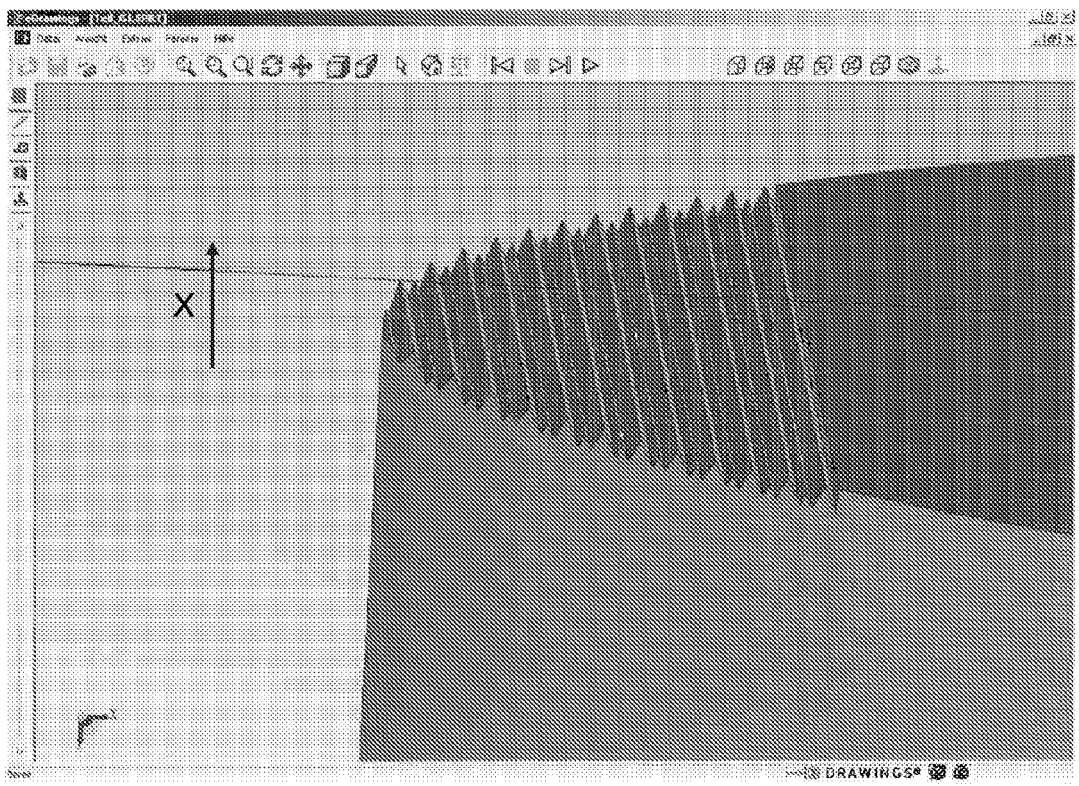
FIG. 2h shows a perspective view on a surface of a substrate according to the second embodiment.

In FIGS. 2a to 2h a second embodiment of the invention is shown in different views. FIG. 2a shows a schematic first perspective view of a second substrate 200 with a second surface 202, FIG. 2b shows a top view, FIG. 2c shows a side view, FIG. 2d shows a cross-sectional view of the intersection line A-A of FIG. 2b, FIG. 2e shows an enlarged detail referred to as "Z" of the cross-section in FIG. 2d, FIG. 2f shows a further enlarged detail referred to as "Y" of the cross-section in FIG. 2e, FIG. 2g shows a further enlarged detail referred to as "X" together with the dimensions and FIG. 2h shows an enlarged perspective view.

The substrate 200 has a diameter D of 1.5 mm. The pattern of the surface structure includes a basic unit of a third elevated structure 206 and a fourth elevated structure 208, which elongates along a first direction x in parallel to the surface 202 as is shown e.g. in FIG. 2h. The cross-section of the third and fourth elevated structure 206, 208 is a triangle. As it is shown in FIG. 2g the cross-section of the third elevate structure is larger than the cross-section of the fourth elevated structure.

The height h3 of the third elevated structure with respect to a nominal surface 210 is chosen as 0.001 mm and, thus, is twice the height h4 of the fourth elevated structure with respect to the nominal surface 210 which is 0.0005 mm. The width w1 of the third elevated structure is chosen as 0.001 mm and the width of the fourth elevated structure is chosen as 0.0005 mm.

Figure 3E:
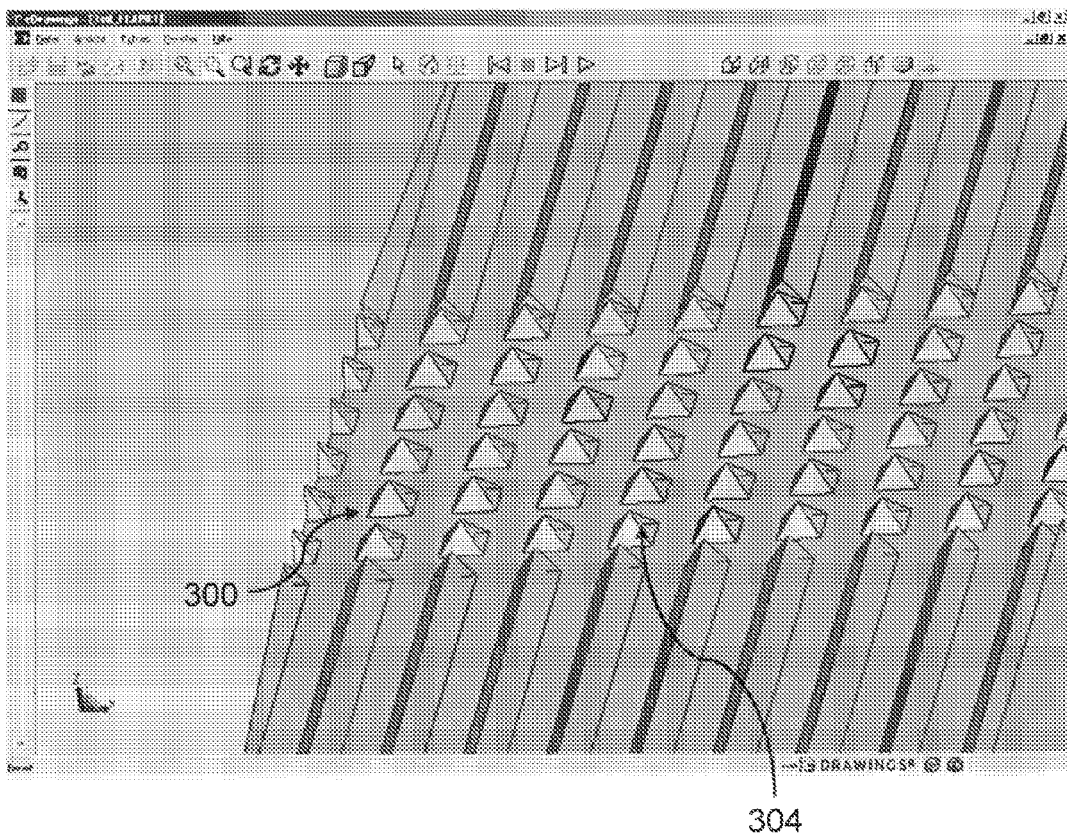
FIG. 3e shows a perspective view on a surface of a substrate according to the third embodiment.

In FIGS. 3a to 3e different views of a third embodiment of the invention are depicted. A third substrate 300 with a third structured surface 302 is shown in a top view in FIG. 3a and in a side view in FIG. 3b. An enlarged detail of the top view in FIG. 3a referred to as "Z" is shown in FIG. 3c and a further enlarged detail of the top view in FIG. 3c referred to as "Y" is shown in FIG. 3d. FIG. 3 shows a perspective view of a surface with a plurality of elevated structures 304.

The elevated structures 304 as a basic unit of the pattern have the form of a pyramid, each, with a square base area and the sidelines of the base areas of different pyramids are arranged in parallel, respectively. The sidelines e.g. might have a width of 0.001725 mm and are spaced apart from each other by a space width of 0.001584 mm. The height of the pyramids with respect to a nominal surface 310 might be chosen to 0.0011 mm.

Figure 4E:
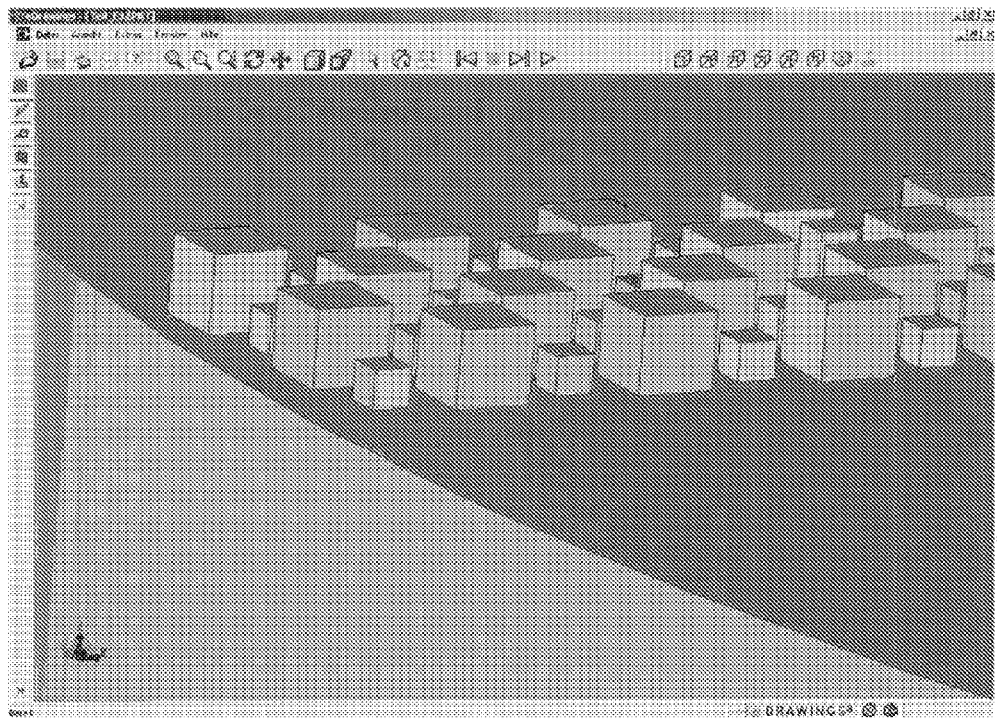
FIG. 4e shows a perspective view on a surface of a substrate according to the fourth embodiment.

In FIGS. 4a to 4e a fourth embodiment is depicted in different views. FIG. 4a shows a top view on a fourth substrate 400 and FIG. 4b the corresponding side view. FIG. 4c shows an enlarged detail referred to as "Z" of the top view in FIG. 4a and FIG. 4d shows an enlarged detail referred to as "Y" of the side view in FIG. 4d. FIG. 4e shows a perspective top view on the surface 402 of the fourth substrate 400.

The pattern used for the fourth embodiment includes a basic unit of a fifth elevated structure and a sixth elevated structure. The fifth and sixth elevated structures are formed as a first cube 404 and a second cube 406 with different volumes. Within the depicted fourth embodiment the sidelines of the first cube 404 are twice as large as the sidelines of the second cube 406 resulting in a volume of the first cube 404 which is eight times the volume of the second cube 406.

The length c1 of the sidelines of the first cube 404 has been chosen to 0.016032 mm and the length c2 of the sidelines of the second cube 406 has been chosen to 0.008016 mm. The pattern is formed from a regular pattern of the first cube 404 and the second cube 406, wherein the first and the second cube are alternately arranged in parallel to a nominal surface 410 surface in a first direction x and a second direction y, which are parallel to the nominal surface 410 and perpendicular to each other.

The sidelines of the first cube 404 and the second cube 406 are arranged in parallel to the first direction x and the second direction y, respectively.

It is also possible to use cuboids with different side lengths instead of or together with cubes in order to build a structured surface.

In FIG. 5 a top view on a target plate 500, comprising a plurality of substrates 502, 504 is depicted. The substrates 502, 504 comprise structured surfaces as explained with respect to the first to fourth embodiment above. On such a target plate a plurality of droplets with different analytes might be applied on a corresponding substrate 502, 504, each.

The substrates 502, 504 might each have the same structured surface or different structured surfaces.

With a plurality of substrates having the same structured surface it is possible to analyze quickly a plurality of different analytes.

With a plurality of different structured surfaces it is possible to analyze the effect of different structured surfaces on the analyzing process.

As is readily apparent for a person skilled at the art the provided dimensions of the elevated structures might be changed for other applications, e.g. other crystallization matrixes. For instance, it is possible to scale the dimensions by a same amount to achieve similar effects.

The embodiments shown include one structured surface, however, as readily apparent for a person skilled at the art it is also possible to use structured surfaces on both, a top and a bottom, surface of a substrate. In addition, also the region 506 between the substrates 502, 504 of the target plate might be structured by e.g. different structures than used on the substrates 502, 504.

Figure 6:
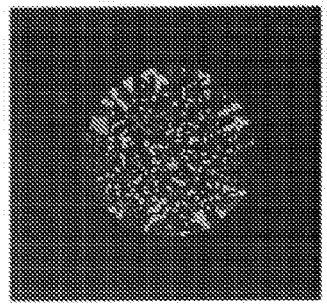
FIG. 6 shows an exemplary table for a comparison between a structured surface and an unstructured surface.
Figure 6:
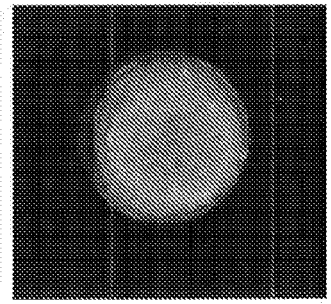

In FIG. 6 a table is shown, which compares the results of microcrystallizations. A drop of 0.5 µl consisting of the same mix of matrix, analyte and solvent has been applied either on an unstructured surface of a polymer substrate that has been coated with diamond-like carbon (middle column) or on a structured surface according to an embodiment of the invention of a polypropylene substrate (left column). The microscope images in the top row of the table show a strong clustering in case of the unstructured surface and a smooth crystallization in case of the structured surface.

With the proposed substrate and the proposed target plate microstructures are proposed that are stimulating smooth crystallization of microcrystals. The substrate and the target plate might also be used for boosting, enhancing, increasing or influencing hydrophobic property of the surface in comparison to an unstructured surface.

Although specific embodiments have been illustrated and described herein, it will be appreciated by those of ordinary skill in the art that a variety of ultra net and/or equivalent implementations may be substituted for the specific embodiments shown and described without departing from the scope of the described embodiments. This application is intended to cover any adaptations or variations of the specific embodiments discussed herein. Therefore, it is intended that this invention be limited only by the claims and the equivalents thereof.

Similar smooth crystallization effects might be achieved when the structure is inverted, i.e. when the structures are not elevated with respect to a nominal surface but are formed as trenches below the nominal surface with the respective cross-sections and dimensions. Thus, the inverted structures might be interpreted as negative images of the elevated structures.

The invention claimed is:

1. A substrate comprising:
    a structured surface including a regular pattern of a plurality of elevated structures that are elevated with respect to a nominal surface of the substrate, the structured surface being configured to stimulate crystallization of microcrystals, wherein
    at least two dimensions of the elevated structures are between 1 nm and 100 µm,
    a basic unit of the regular pattern includes a first elevated structure which is elongated along a first direction in parallel to the nominal surface and which includes a first cross-section perpendicular to the first direction and the regular pattern further includes a second elevated structure, which is elongated along the first direction and which includes a second cross-section perpendicular to the first direction, such that the second cross-section is smaller than the first cross-section, a height of the first cross-section perpendicular to the nominal surface is different from a height of the second cross-section perpendicular to the nominal surface, in the regular pattern, a first distance between the first elevated structure and the second elevated structure is different from a second distance between the second elevated structure and a next first elevated structure, the first distance being half the second distance so as to stimulate crystallization of the microcrystals, and the first distance and the second distance are determined based on at least one of a size, crystallization form, and shape of the microcrystals.

2. The substrate according to claim 1, wherein the first cross-section and the second cross-section are squares.

3. The substrate according to claim 1, wherein
the first distance and a first side of the second cross-section are equal in length, and
the second distance and a first side of the first cross-section are equal in length.

4. A substrate comprising:
a structured surface including a regular pattern of a plurality of elevated structures that are elevated with respect to a nominal surface of the substrate, the structured surface being configured to stimulate crystallization of microcrystals, wherein
at least two dimensions of the elevated structures are between 1 nm and 100 µm,
a basic unit of the regular pattern includes a first elevated structure which is elongated along a first direction in parallel to the nominal surface and which includes a first cross-section perpendicular to the first direction and the regular pattern further includes a second elevated structure, which is elongated along the first direction and which includes a second cross-section perpendicular to the first direction, such that the second cross-section is smaller than the first cross-section,
areas of the first and second cross-sections are essentially equal throughout each respective elevated structure,
a height of the first cross-section perpendicular to the nominal surface is different from a height of the second cross-section perpendicular to the nominal surface,
in the regular pattern, a first spacing between the first elevated structure and the second elevated structure is different from a second spacing between the second elevated structure and a next first elevated structure, the first spacing being half of the second spacing so as to stimulate crystallization of the microcrystals, and
the first spacing and the second spacing are determined based on at least one of a size, crystallization form, and shape of the microcrystals.

5. The substrate according to claim 4, wherein
the height of the first cross-section perpendicular to the nominal surface is twice the height of the second cross-section perpendicular to the nominal surface.

6. A substrate comprising:
a structured surface including a regular pattern of a plurality of elevated structures that are elevated with respect to a nominal surface of the substrate, the structured surface being configured to stimulate crystallization of microcrystals, wherein
at least two dimensions of the elevated structures are between 1 nm and 100 µm,
a basic unit of the regular pattern includes a first elevated structure with a first volume and a second elevated structure with a second volume, the second volume being smaller than the first volume,
a height of the first elevated structure perpendicular to the nominal surface is different from a height of the second elevated structure perpendicular to the nominal surface,
in the regular pattern, a first spacing between the first elevated structure and the second elevated structure is different from a second spacing between the second elevated structure and a next first elevated structure, the first spacing being half of the second spacing so as to stimulate crystallization of the microcrystals, and
the first spacing and the second spacing are determined based on at least one of a size, crystallization form, and shape of the microcrystals.

7. The substrate according to claim 6, wherein
the first and the second elevated structures are cubes.

8. The substrate according to claim 6, wherein
the second volume is eight times smaller than the first volume.

9. The substrate according to claim 8, wherein
the height of the first elevated structure perpendicular to the nominal surface is twice the height of the second elevated structure perpendicular to the nominal surface.

10. The substrate according to claim 6, wherein
the basic unit of the first elevated structure and the second elevated structure is repeated in a first direction in parallel to the nominal surface of the substrate and in a second direction in parallel to the nominal surface and perpendicular to first direction.

11. The substrate according to claim 10, wherein
side faces of the first elevated structure and the second elevated structure are arranged in parallel to the first direction and the second direction, respectively.

12. The substrate according to claim 1, wherein
the at least two dimensions are between 1 nm and 50 µm.

13. The substrate according to claim 12, wherein
the at least two dimensions are between 1 nm and 2 µm.

14. The substrate according to claim 1, wherein
the elevated structures are inverted and formed as trenches below the nominal surface.

15. A target plate comprising
a plurality of substrates according to claim 1.

16. The substrate according to claim 1, wherein
the height of the first cross-section perpendicular to the nominal surface is twice the height of the second cross-section perpendicular to the nominal surface.

17. The substrate according to claim 4, wherein
the at least two dimensions are between 1 nm and 50 µm.

18. The substrate according to claim 6, wherein
the at least two dimensions are between 1 nm and 50 µm.

19. The substrate according to claim 4, wherein
the elevated structures are inverted and formed as trenches below the nominal surface.

20. The substrate according to claim 6, wherein
the elevated structures are inverted and formed as trenches below the nominal surface.

21. A target plate comprising a plurality of substrates according to claim 4.

22. A target plate comprising a plurality of substrates according to claim 6.

23. The substrate according to claim 1, wherein
the first distance and the second distance are between 1 nm and 1 µm.

24. The substrate according to claim 4, wherein
the first spacing and the second spacing are between 1 nm and 1 µm.

25. The substrate according to claim 6, wherein
the first spacing and the second spacing are between 1 nm and 1 µm.

* * * * *